United States Patent [19]
Sugerman

[11] Patent Number: 5,938,626
[45] Date of Patent: Aug. 17, 1999

[54] APPARATUS FOR LOWERING INTRA-ABDOMINAL PRESSURE

[75] Inventor: Harvey J. Sugerman, Richmond, Va.

[73] Assignee: Virginia Commonwealth University, Richmond, Va.

[21] Appl. No.: 09/121,600

[22] Filed: Jul. 24, 1998

[51] Int. Cl.$^6$ ................................................ A61B 17/42
[52] U.S. Cl. ............................... 601/6; 601/11; 600/561; 600/568; 606/121
[58] Field of Search ....................... 128/202.12; 600/561, 600/588; 601/6, 10, 11, 43, 44; 606/123, 121

[56] References Cited

U.S. PATENT DOCUMENTS

| | | |
|---|---|---|
| 230,351 | 7/1880 | Seyberlich . |
| 726,791 | 4/1903 | Armbruster . |
| 1,498,430 | 9/1924 | Doerfler . |
| 2,490,395 | 3/1949 | Wilm . |
| 2,597,637 | 8/1952 | Heidenwolf . |
| 2,917,050 | 11/1959 | Kenyon . |
| 3,062,215 | 11/1962 | Heyns . |
| 3,642,006 | 2/1972 | Wobbe ..................................... 606/121 |
| 3,988,793 | 11/1976 | Abitbol . |
| 4,014,344 | 3/1977 | Gutierrez . |

FOREIGN PATENT DOCUMENTS 1180932   2/1970   United Kingdom .

OTHER PUBLICATIONS

Scott, et al., A Method of Abdominal Decompression in Labor; The Lancet; May 28, 1960; pp. 1181–1183.

Heyns, Abdominal Decompression in the First Stage of Labour; Journal of Obstetrics and Gynaecology; vol. 66, pp. 220–228, 1959.

Heyns, et al., Influence of Abdominal Decompression on Intra–Amniotic Pressure and Fetal Oxygenation; The Lancet; Feb. 10, 1962, pp. 289–292.

Blecher, et al., Treatment of the Toxemias of Pregnancy; The Lancet; Sep. 23, 1967, pp. 621–625.

Coxon, et al., The Effects of Abdominal Decompression on Vascular Haemodynamics in Pregnancy; The Journal of Obstetrics and Gynaecology of the British Commonwealth; vol. 78, pp. 49–54, 1971.

MacRae, et al., Clinical and Endocrinological Aspects of Dysmaturity and the use of Intermittent Abdominal Decompression; The Journal of Obstetrics and Gynaecology of the British Commonwealth; vol. 78, pp. 636–641, Jul. 1971.

Varma, et al., The Effects of Abdominal Decompression on Pregnancy Complicated by the Small–For–Dates Fetus; The Journal of Obstetrics and Gynaecology of the British Commonwealth, vol. 80, pp. 1086–1094, Dec., 1973.

Hofmeyr, et al., Abdominal Decompression: new data from a previous study; British Journal of Obstetrics and Gynaecology; vol. 97, pp. 547–548; Jun. 1990.

Hofmeyr, Abdominal Decompression During Pregnancy; Effective Care in Pregnancy and Childbirth, pp. 647–652; 1989.

(List continued on next page.)

*Primary Examiner*—John Mulcahy
*Attorney, Agent, or Firm*—Whitham, Curtis & Whitham

[57] ABSTRACT

An abdominal decompression apparatus reduces intra-abdominal pressure in patients by application of negative pressure to the patient's abdomen. Preferably, the negative pressure is applied continuously at low negative pressures (e.g., –20 to –40 mm Hg) for extended periods of time (e.g., 6–12 hours). Changes in the patient's intra-abdominal pressure can be monitored using measurements of the patient's bladder pressure, and treatments can be designed to achieve desired decreases in bladder pressure. To alleviate pain and permit maximum decrease in intra-abdominal pressure, a countertraction mechanism is connected to the shell which encloses the patient's abdomen, and counters the negative pressure induced downward movement of the shell on the patient's chest. The countertraction mechanism is sufficient to reduce or eliminate the negative pressure induced downward movement but is less than an amount which would cause loss of vacuum pressure within said shell.

11 Claims, 4 Drawing Sheets

OTHER PUBLICATIONS

Hofmeyr, et al., Should Abdominal Decompression be Consigned to the History of Books?; British Journal of Obstetrics and Gynaecology, vol. 97, pp. 467–469, Jun. 1990.

Shimonovitz, et al., Intermittent Abdominal Decompression: an Option for Prevention of Intrauterine Growth Retardation; British Journal of Obstetrics and Gynaecology, vol. 99, pp. 693–695, Aug., 1992.

Quinn, et al., Abdominal Decompression During the First Stage of Labour; American Journal of Obstetrics and Gynecology; vol. 83, No. 4, pp. 458–463, Feb., 1962.

Quinn, et al., Experiences with Abdominal Decompression During Labour; American Journal of Obstetrics and Gynecology, vol. 71, No. 6, pp. 934–939, Dec. 1964.

APPARATUS FOR LOWERING INTRA-ABDOMINAL PRESSURE

CROSS-REFERENCE TO RELATED APPLICATIONS

This application is related to U.S. patent application Ser. No. 08/724,248, filed Sep. 30, 1996, and U.S. patent application Ser. No. 08/648,508, filed May 15, 1996, and the complete contents of these two applications is herein incorporated by reference.

DESCRIPTION

BACKGROUND OF THE INVENTION

1. Field of the Invention

The invention is generally related to medical devices used for lowering intra-abdominal pressure (IAP)in patients. More particularly, the invention pertains to a device which is more comfortable to the patient and which reduces or eliminates pain on the lower rib cage of the patient.

2. Description of the Prior Art

Abdominal decompression has been investigated for a number of years in connection with the treatment of pregnant women. Specifically, studies have been conducted to evaluate the ability of abdominal decompression to ease the pain of labor, to increase intra-uterine fetal growth, or treat toxemia of pregnancy. In all previous investigations, abdominal decompression was performed intermittently at high negative pressures for short periods of time (e.g., −70 mm Hg for 30 seconds every minute for 30 minutes, twice daily).

Heyns, *Obstet. Gynaecol. Br. Commonw.*, 66: 220–228, 1959, discloses a study wherein intermittent abdominal decompression is used for the treatment of labor pains during the first stage of labor. Eight patients were used in the study, and the patients controlled the negative pressure themselves by placing a finger over a vent tube to bring the pressure down to around 50 mm Hg in most instances for about sixty seconds. However; in some cases the pressure was brought down to as low as 150 mm Hg. The article reports that the labor pains were relieved in all eight patients, and that the treatment did not interfere with diagnosing the second stage of labor (actual commencement of delivery).

Heyns et al., *Lancet*, 1: 289–292 (1962), present data from a study using intermittent abdominal decompression for thirty minutes on twelve or more occasions in 350 caucasion women during the last two months of pregnancy and during labor. In the study, amniotic fluid pressure was measured and it was found that this pressure rose to 40 mm Hg during early labor, and 50–70 mm Hg during mid-labor as the second stage approached. It was found that abdominal decompression lowered these pressures to zero or less at the height of a uterine contraction. The highest pressures were found in the small primigravida with a tight belly wall and in active athletes. The fetal heartbeat did not change in rate during uterine contractions with decompression. The placenta from women treated with decompression was reported to have a richer arteriolar and capillary network. In a non-randomized study, the perinatal death rate in babies subjected to decompression was 0.6%, compared to 3% to a non-treated group. The authors concluded that the data suggests that decompression improves fetal oxygenation.

There have been two other studies using intermittent abdominal decompression for the first stage of labor by Quin, L J et al., which are found in *Amer. J Obstet. Gynecol.* 83: 458, 1962, and *J. Obstet. Gynaecol.* 71: 934, 1964. The device was used in 100 primiparas and 42 multiparas in the first study and 302 primiparas and 188 multiparas in the second study, and there was an 86% excellent or good pain relief response with its use. The device was modified with a switch to the vacuum pump which the patient activated at the onset of labor pain and turned off at the completion of a contraction. This device was manufactured by the J. H. Emerson Co., Cambridge, Mass., and called the "Birtheez".

Blecher et al., *Lancet*, 2: 621–625, 1967, reports on a study with fifty caucasion and 80 non-white patients treated by abdominal decompression applied for ten minutes twice on the first day of treatment, twenty minutes twice on the second day of treatment, and thirty minutes twice on the third and subsequent days of treatment. Toxemia of pregnancy was hypothesized to be secondary to uterine ischemia produced by increased IAP, and that abdominal decompression would prevent this ischemia and prevent or correct toxemia. The pressures used in the study were individually gauged according to the patients' tolerance, and were generally between −50 and −80 mm Hg for 15 seconds in every half minute. It was reported that the treated patients whose hypertension was secondary to toxemia had a significantly better response, and that they had a significantly better fetal survival rate.

Coxon et al., *J. Obstet. Gynaecol. Br. Commonw.*, 78: 49–54, 1971, reports on a study wherein the authors used the radioisotope indium 113 m bound to transferrin and an external counter and observed a 30% increase in placental count rate with abdominal decompression. The use of abdominal decompression during a uterine contraction in the first stage of labor resulted in a 15% increase in placental site count rate over the uterine wall away from the placental site. The authors apparently used test conditions where approximately −70 mm Hg abdominal decompression was applied, but the frequency and duration were not provided. The Coxon et al. study appears to support the Heyns hypothesis that abdominal decompression improves fetal blood flow.

Macrae et al., *J. Obstet. Gynaecol. Br. Commonw.*, 78: 636–641. 1971, reports on a study where intermittent abdominal decompression (negative pressure of −70 mm Hg applied for fifteen seconds of every minute over a ½ hour period, with treatment sessions ranging from 2–3 times per week) was asserted to raise estriol levels to normal. Dysmaturity, which is associated with a high perinatal mortality, is associated with decreased estriol levels.

Varma et al., *J. Obstet. Gynaecol Br. Commonw.*, 80: 1086–1094, 1973, studied intermittent abdominal decompression in 70 pregnant patients with "small-for-dates" fetuses as compared to 70 similar control cases. The decompression group received abdominal decompression once a day in the Heyns decompression suit in which they were placed for thirty minutes using a negative pressure of 80–90 mm Hg for 25 seconds every minute. Ultrasound cephalometry and 24 Hr urinary estrogen levels were measured. The mean fetal growth rate of the decompression group was significantly greater than the untreated group and was associated with a significantly higher estrogen excretion and lower incidence of fetal distress as well as a significantly higher Apgar score and a lower percent of low birth weight babies and perinatal mortality.

Hofmeyr, "Abdominal decompression during pregnancy", in *Effective Care in Pregnancy and Childbirth*, Chalmers I, Enkin M, Keirse MJNC, eds., Oxford University Press, Oxford, 1989, pp. 647–652, provides a review of the literature on abdominal decompression and describes the apparatus, the technique, and indications for its use. However, it is concluded that: "There is some evidence that abdominal decompression may be of value in certain abnormal states of pregnancy but the studies reported to date are not of sufficient methodological quality to support the use of abdominal decompression except within the context of further methodologically sound, controlled trials. Nevertheless, there are so few options for managing the compromised fetus other than elective delivery that it is important to subject abdominal decompression to further evaluation."

Hoffmeyr et al., Er. J. Obstet. Gynaecol., 97: 547–548, 1990, provided a further evaluation of a previous randomized controlled trial designed to test the hypothesis that higher developmental quotients would develop in infants born to mothers treated with intermittent abdominal decompression secondary to improved fetal blood flow. The patients were randomized to treatment or control groups, and the treated group received abdominal decompression three times per week from thirty weeks of gestation using patient controlled decompression for fifteen seconds each minute over thirty minutes. No differences in gestation time, birthweight at delivery or one minute Apgar scores were noted between the groups.

In an editorial, Hofmeyr, Br. J. Obstet. Gynaecol., 97: 467–469, 1990, suggests that the negative reaction to the failure of abdominal decompression to improve fetal development scores or intelligence quotients in normal pregnancies, as initially suggested by Heyns, may detract from its possible benefits to decrease the pain of labor and fetal distress, or treat toxemia or poor fetal growth which may be secondary to impaired placental blood flow.

Shimonovitz et al., Er. J. Obstet. Gynaecol., 99: 693–695, 1992, describe three women with a "bad obstetric history", e.g., multiple recurrences of toxemia, severe intrauterine growth retardation, and fetal death, who were treated with intermittent abdominal decompression (−70 mm Hg for thirty seconds every minute for thirty minutes, two times a day) with excellent results including correction of hypertension and improved fetal growth.

SUMMARY OF THE INVENTION

It is an object of this invention to provide a method and apparatus for lowering intra-abdominal pressure which can be used in the treatment of a wide variety of disorders such as those which are associated with acute abdominal compartment syndrome, increased intra-abdominal pressure related morbidity in severely obese individuals, and pre-eclampsia in pregnancy.

It is another object of this invention to provide a treatment regime for head injuries and for patients suffering from space occupying brain lesions wherein the intra-abdominal pressure of the patient is lowered such that intracranial pressure is caused to be lowered.

It is another object of this invention to provide a method and apparatus for lowering intra-abdominal pressure which provides relatively low levels of negative pressure (e.g., −20 to −45 mm Hg) to a patient's abdomen, on a continuous basis, for extended periods of time.

It is yet another object of this invention to provide a method and apparatus for lowering intra-abdominal pressure in a patient that utilizes urinary bladder pressure measurements of the patient to control intensity and treatment duration.

It is still another object of this invention to provide a method and apparatus for lowering intra-abdominal pressure in a patient that is less painful during use.

It is yet another object of this invention to provide a counter-traction mechanism for an apparatus for lowering intra-abdominal pressure.

According to the invention, a patient's intra-abdominal pressure is advantageously lowered by providing abdominal decompression to the patient on a continuous basis for an extended period of time. The abdominal decompression device can be constructed in a variety of forms with the principal object being to apply negative pressure at the site of the patient's chest and abdomen. The abdominal decompression device will preferably either have an air tight suit positioned over a rigid frame which is spaced approximately 4–6 inches away from the patient's chest and abdomen; or, alternatively, will include a rigid dome vest made of plastic or other suitable materials which will be held in place on the patient's chest and abdomen. In the case of a rigid dome vest, a material which traverses around the patient's back that is connected using clips or hook and loop connecters (Velcro®) or other suitable connectors can be used to hold the dome in place, or it may be self-sealing when a vacuum is applied.

A pump is connected to the air tight suit or dome vest and is used to apply negative pressure in the space between the suit or vest and the patient. A gauge is connected to the line connected to the pump for aiding in regulating the vacuum pressure inside the abdominal decompression device.

It has been observed that a failing of prior abdominal decompression devices is that the pressure is often too high to be comfortable (e.g., 100–150 mm Hg), and is often not regulated (e.g., patient applied finger on a vent tube). The method and apparatus of this invention is directed to providing a low vacuum pressure (e.g., 20–45 mm Hg) which can be tolerated by a patient for an extended period of time. Preferably, the abdominal decompression device will be worn for six to twelve hours, and most preferably overnight for eight hours while the patient is sleeping. In addition, unlike prior art devices, the method and apparatus of this invention contemplates the application of continuous, as opposed to intermittent, negative pressure on the patient's chest and abdomen. The prolonged, continuous, low negative pressure treatment provides a more reliable mechanism for reducing intra-abdominal pressure than prior devices which rely on high pressures for intermittent time periods.

Another failing of prior art abdominal decompression devices is that they do not provide any means of determining the intra-abdominal pressure of the patient during treatment. The method and apparatus of this invention contemplate using the patient's urinary bladder pressure as an assessment of intra-abdominal pressure. It has been found that in most clinical situations urinary bladder pressure accurately reflects intra-abdominal pressure. The urinary bladder pressure measurement can be determined using a Foley catheter or other suitable device, and would preferably be left in place during the initial application of vacuum pressure to the patient's chest and abdomen.

Still another failing of prior art abdominal decompression devices is that they have been designed without the realization that suction produced in a compartment above the patient's chest not only pulls the abdomen up, but also pulls the compartment against the patient's chest. This can result in pain for the patient in areas contacted by the compartment edges (e.g., the lower rib cage and pelvis). In addition, the action of pulling the compartment inward toward the patient can result in inadequate lowering of intra-abdominal pressure since it acts as a limitation to the relief of intra-abdominal pressure. Therefore, an important feature of this invention is to provide a mechanism which will counteract the inward pulling forces during application of negative pressure inside the compartment, but which will still permit a tight seal over the patient's chest allowing the negative pressure to act primarily to pull the patient's abdomen upwards. In the preferred embodiment of this invention, progressively increasing levels of force can be applied to counteract progressively increasing amounts of inward pulling forces exerted during application of vacuum pressure within the compartment. In one embodiment, a pulley mechanism is connected to the compartment, and allows the application of increasing amounts of weight thereto for countering the inward pulling forces exerted during application of vacuum pressure within the compartment. Countering the inward pulling forces during application of negative pressure reduces or eliminates pressure pain on the lower rib cage and pelvic bones, and produces further decreases in urinary bladder pressure.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1A:
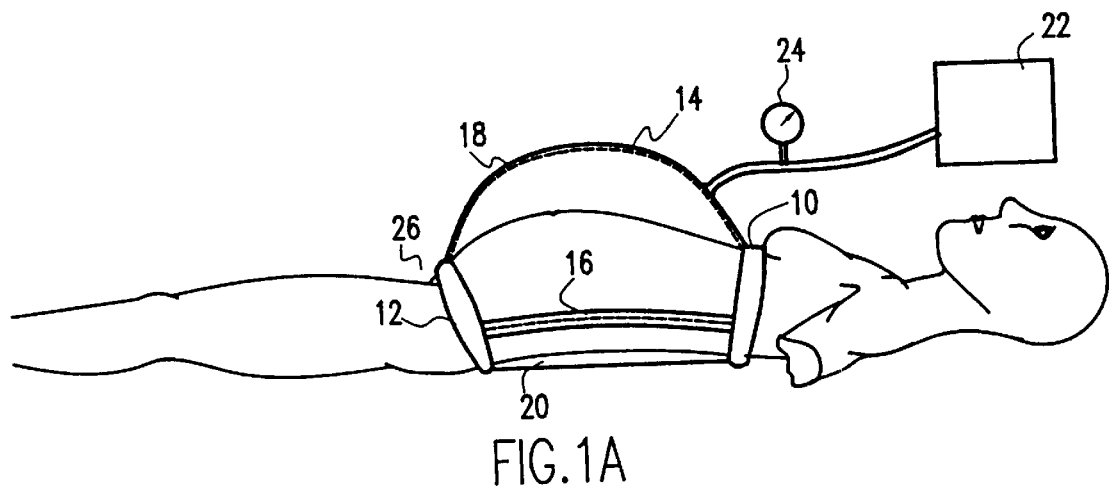
FIGS. 1a and 1b show side and top schematic views of a patient positioned in an abdominal decompression device of the present invention.

Clinical and animal studies have demonstrated that increased intra-abdominal pressure (IAP) produces elevated renal venous and inferior vena caval pressure, and these conditions cause the kidneys to leak protein to produce hormones which increase systemic blood pressure. The increased IAP also pushes the diaphragm cephalad, "squeezing" the lungs, interfering with respiratory function, and raising intra-thoracic pressure. This impairs venous return from the brain, raising intracranial pressure, as well as impairs return from the liver, interfering with the intestinal venous drainage and causing liver vascular engorgement, leading to the risk of hepatic rupture in the case of eclampsia.

Lowering IAP can be useful for the treatment of pre-eclampsia and toxemia of pregnancy, decreasing the pain of labor, and improving intra-uterine fetal growth. However, for more effective treatment than has been achieved with previous investigative devices, a more gradual decrease in negative pressure is required. This allows the pressure reducing device to be more easily tolerated by the patient and to be "worn" or "used" for extended periods of time (e.g., 6–12 hours, such as eight hours overnight while sleeping). The prolonged treatment provides a significantly enhanced effect on lowering IAP, not heretofore observed in previous investigations.

Furthermore, the method and apparatus of this invention can be used for treating a number of different conditions. For example, increased IAP in severely obese individuals can result in obesity hypoventilation syndrome, obesity related diabetes as well as gestational diabetes, chronic venous stasis ulcers or edema (e.g., lower extremity), idiopathic intracranial hypertension (pseudotumor cerebri), systemic hypertension secondary to obesity, nephrotic syndrome of obesity, and gastro-esophageal reflux. These disorders which stem from the patient's obese condition can be treated or alleviated with a prescribed program for reducing IAP. In addition, "Acute Abdominal Compartment Syndrome" is often seen in critically ill medical or surgical patients where there is an acute increase in IAP, and this syndrome may cause kidney and lung failure, infarction of the intestine, or marked increases in brain cerebrospinal fluid pressure. Patients suffering from acute abdominal compartment syndrome should benefit from applying a negative pressure continuously in the intensive care unit or other treatment setting for as long as the IAP is elevated.

Patients with head injuries or cerebral space occupying lesions can be treated by lowering intra-abdominal pressure using the method and apparatus of this invention. Lowering intra-abdominal pressure lowers intrapleural pressure, thus improving venous draining and ultimately lowering intracranial pressure. By lowering the intracranial pressure the patient's condition will be improved.

Those skilled in the art will recognize that other disorders stemming from or associated with elevated IAP would benefit from a program and device designed to reduce IAP to normal levels. For example, the method and apparatus of this invention may also be useful in the treatment of obesity related Type II diabetes mellitus and sleep apnea syndrome.

In a preferred embodiment of this invention, the urinary bladder pressure is utilized to estimate and monitor changes in IAP. It has been found that urinary bladder pressure measurements accurately reflect IAP in most clinical situations. Studies have shown that the average urinary bladder pressure in morbidly obese patients is 18±0.7 (range 12 to 42) cm $H_2O$, while non-obese patients have a urinary bladder pressure of 7.1±1.6 cm $H_2O$. In addition, clinical studies have shown that the urinary bladder pressure is between 20–30 cm $H_2O$ during the third trimester of pregnancy. The apparatus of this invention would be used to apply negative pressure on the patient's abdomen until such time as the urinary bladder pressure measurements are more closely associated with those found in non-obese patients (e.g., 10–14 cm $H_2O$) Preferably the target urinary bladder pressure measurement would be selectable by the physician, and would be chosen to be clinically effective for the condition or syndrome being treated. By using bladder pressure measurements of the patient under treatment to control the intensity and duration of treatment with the negative pressure device, the IAP of the patient can be continuously monitored during treatment without the need for intermittent breaks in negative pressure to evaluate IAP by other means.

Figure 1B:
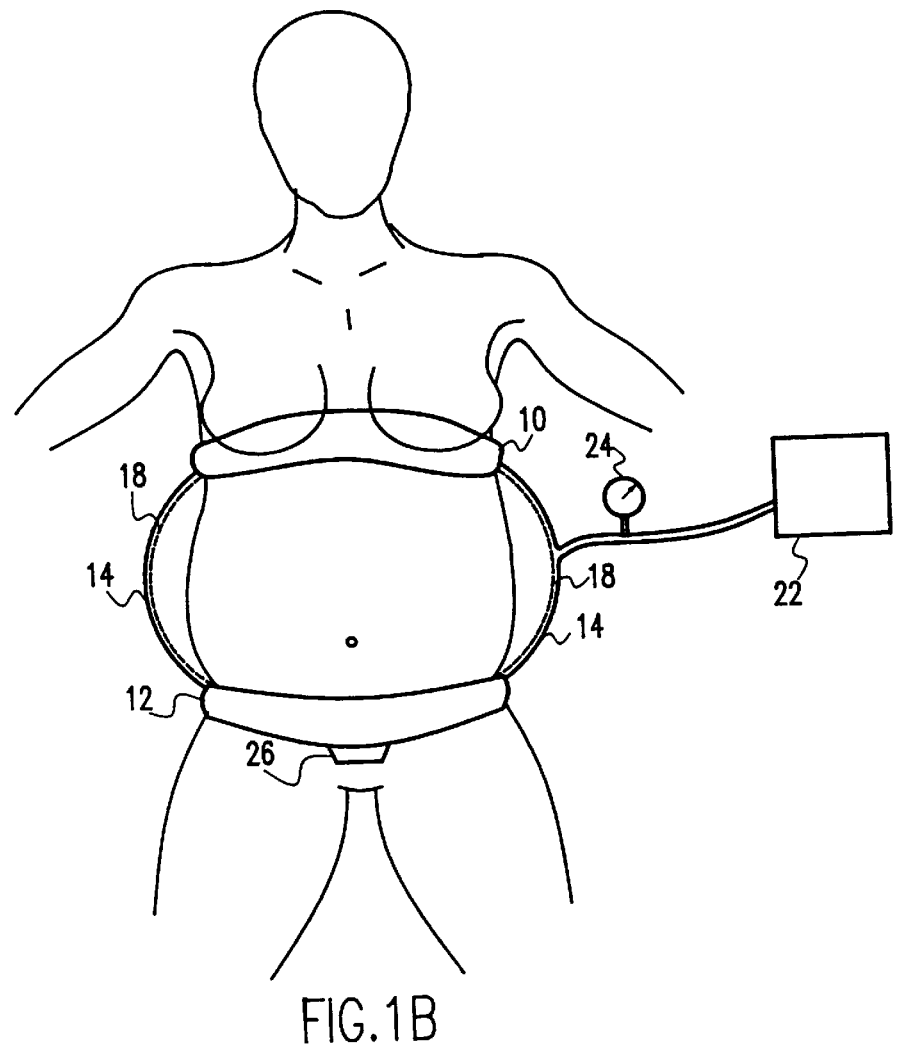

FIGS. 1a and 1b schematically show one example of an abdominal decompression system according to the present invention. Inflatable cuffs 10 and 12 are secured at the chest and pelvis of the patient being treated. Cuffs 10 and 12 are intended to maintain an air tight enclosure; therefore, body contacting surfaces may be provided with features intended to promote air tight connections. For example, silicone oil may be applied and held within recessed regions (not shown) on the body contacting surfaces of the cuffs 10 and 12, or the body contacting surfaces of the cuffs 10 and 12 could include pocket regions designed to prevent ambient air from being suctioned under the cuffs 10 and 12. While the preferred abdominal decompression device utilizes inflatable cuffs 10 and 12 because of the advantages of being lightweight and conformable to the contours of the patient's body, other materials such as neoprene rubber or the like might be used for the cuffs 10 and 12. Or even more simply, a drawstring can by used to cinch the material around the patient's chest and pelvis.

Furthermore, while FIGS. 1*a–b* show a cuff 12 placed at the pelvis, it should be understood that the abdominal decompression device could be "sack-shaped", including only one cuff 10 positioned at the patient's chest and extending therefrom to cover the wearer's legs.

An air tight enclosure 14 is positioned between cuffs 10 and 12. The air tight enclosure 14 can be made of plastic, nylon®, goretex®, or other suitable materials. In the case of a single cuff 10 design, the air tight enclosure 14 would extend over the patient's legs and feet. An air tight zipper 16 could be provided for easier patient access into the abdominal decompression device. Alternatively, a non-zippered overlap enclosure could be provided which self-seals with the application of negative pressure.

A frame with multiple perforations 18, preferably made of metal, plastic, or other rigid materials is positioned under the air tight enclosure 14 and is used to support the air tight enclosure slightly above the patient's chest and abdomen, but sufficient to provide access for the application of negative pressure. A preferred distance for the frame 18 to hold the enclosure 14 above the patient's chest and abdomen is two to six inches. The frame 18 may advantageously encircle three quarters of the patient's body and be positioned on the mattress of a bed or be affixed to a back support 20 on which the patient rests during treatment. The back support can be made from any suitable material and should provide the patient with comfort during extended periods of wear either in bed or in a chair.

Negative pressure is applied in the space between the frame 18 and the abdomen using a vacuum source 22. The air tight enclosure 14 on top of the frame 18 allows the negative pressure environment around the patient's chest and abdomen to be generated by the vacuum source 22. The vacuum source could be a variable vacuum pump, an AC pump or a DC pump, or any other suitable device which can evacuate air from between the frame 18 and patient's chest and abdomen A pressure gauge 24 is provided to monitor the negative pressure being applied. In the preferred embodiment of this invention, a constant negative pressure of approximately –20 to –45 mm Hg is exerted by vacuum source 22, and the pressure is applied continuously for an extended treatment period. In most cases, it is anticipated that the treatment period will be six to twelve hours (e.g., approximately eight hours overnight); however, it should be understood for certain conditions longer or shorter periods might be more clinically appropriate. In addition, the amount of negative pressure is ideally low (e.g., –20 to –45 mm Hg in most applications) since higher negative pressures are generally uncomfortable to patients for extended periods of time; however, for certain conditions, higher or lower pressures may be useful for clinical effectiveness.

Figure 2A:
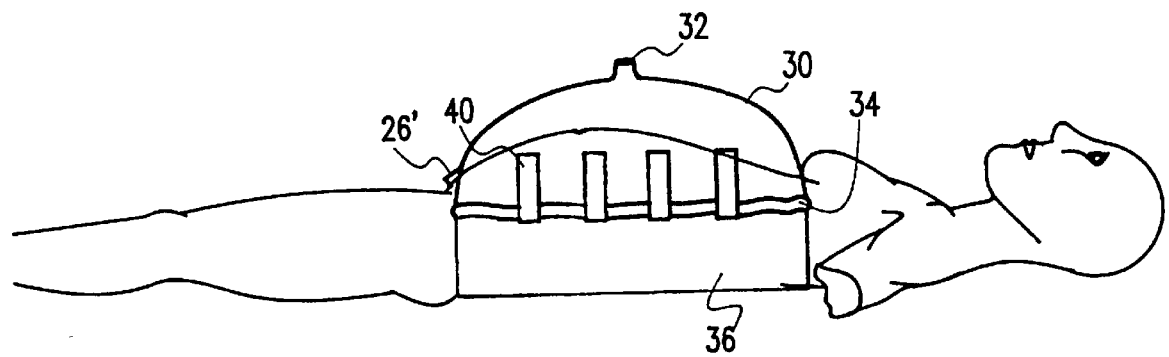
FIGS. 2a and 2b show side and top schematic views of a domed vest for abdominal decompression according to the present invention.
Figure 2B:
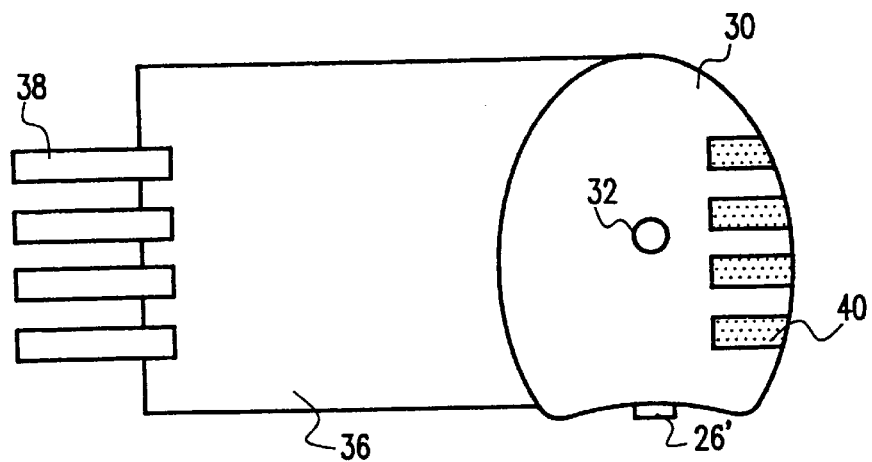

FIGS. 2*a* and 2*b* show an alternative design for the abdominal decompression device according to the present invention. In FIGS. 2*a* and 2*b,* a rigid dome 30 is placed over the patient's chest and abdomen. The dome 30 extends above the patient and defines a cavity which can be used to apply negative pressure to the patient's chest and abdomen.

Vacuum pressure is applied to the cavity through port 32. The dome 30 can be made of a plastic, fiberglass, metal or other suitable materials, and should be of sufficient rigidity to withstand deforming under the pressure of the applied vacuum (e.g., preferably 20 to –45 mm Hg as discussed above in connection with FIGS. 1*a* and 1*b*). An air tight seal 34, such as a foam rubber gasket or other suitable material, will seal the dome 30 against the patient's chest and abdomen. The dome 30 will be held in place using either an attached posterior vest 36 or by straps which extend from one side of the dome 30 around the patient's back and is connected to the opposite side of the dome 30 using connectors 38 and 40 which may be Velcro® strips, clips tape, straps with punch holes for connection to a belt-type connector, or other suitable devices. Alternatively, the shell may fit in a way to "self-seal" so that straps are not required. The abdominal decompression device of FIGS. 2*a* and 2*b* has the advantage of enabling the patient to get in and out of the device more easily than the design shown in FIGS. 1*a* and 1*b*.

In either embodiment the shell of the intra-abdominal pressure device is preferably designed to be 10 to 20 cm above the patient's abdomen so that, should an excessive negative pressure be applied, intentionally or by accident, the abdominal wall cannot be raised further and, therefore, there cannot be an excessive reduction in intra-abdominal pressure which could lead to serious cardiovascular complications. Thus, the device has a self-protective mechanism which obviates the need for an automatic "shut-off switch" on the negative pressure pump. As the shell is restricted by the chest component (i.e., it is designed to be applied below the breasts) and the pubic bone, it is also prevented from migrating toward the back, so that the space above the abdomen remains fixed.

Urinary bladder pressure detection system, shown as element 26 in FIGS. 1*a–b* and element 26' in FIGS. 2*a–b,* provides measurements of the patient's urinary bladder pressure. The detection system 26 or 26' can take the form of a urinary Foley catheter or another suitable device. As discussed above, it has been found that the patient's urinary bladder pressure accurately reflects the intra-abdominal pressure of the patient being treated. The normal bladder pressure in non-obese individuals averages approximately 7 cm $H_2O$, whereas the bladder pressure is considerably elevated (e.g., 15–42 cm $H_2O$) in severely obese patients, in patients suffering from acute abdominal compartment syndrome, and in patients with complicated pregnancies.

The bladder pressure measurement should provide an effective mechanism for controlling the treatment regimen of a patient suffering from elevated IAP in a number of different situations. For example, in critically ill patients suffering from the acute abdominal compartment syndrome, the abdominal decompression device can be fitted onto the patient and the duration of the negative pressure and amount of negative pressure applied can be controlled in a manner which achieves a pre-selected level of bladder pressure. That is, treatment continues until halted by a physician or the pre-selected level is reached. A computer controller (not shown) could be affixed to the bladder pressure detection system 26 or 26' and vacuum source 22 to control the amount of vacuum in the compartment enclosed based on bladder measurements. This would allow automatic adjustment of vacuum pressure in accordance with changes in bladder pressure measurement and automatic cut-off when desired target levels are reached. In severely obese patients or in pregnant patients, a pre-selected time of negative pressure application can be used, with the bladder pressure measurements providing feedback on the effectiveness of the treatment.

Recent experiments with the devices similar to that shown in FIGS. 1a–b and 2a–b have demonstrated that the negative pressure exerted in the patient containing compartment by the vacuum source 22 not only pulls the patient's abdomen up, but also pulls the shell (i.e., dome 30) into the patient's abdomen and chest so that it caused pain on the lower rib cage and pelvis. In addition, this downward movement of the shell also results in a failure to lower urinary bladder pressure adequately in some patients.

It has been found that providing a mechanism to counteract the downward pulling force of the shell against the patient, but retaining the tight seal of the shell against the patient to thereby allow upward pulling of the patient's abdomen under vacuum pressure can both reduce or eliminate pressure pain on the lower rib cage and pelvic bones, and produce a further decrease in urinary bladder pressures (see Example 7).

Figure 3A:
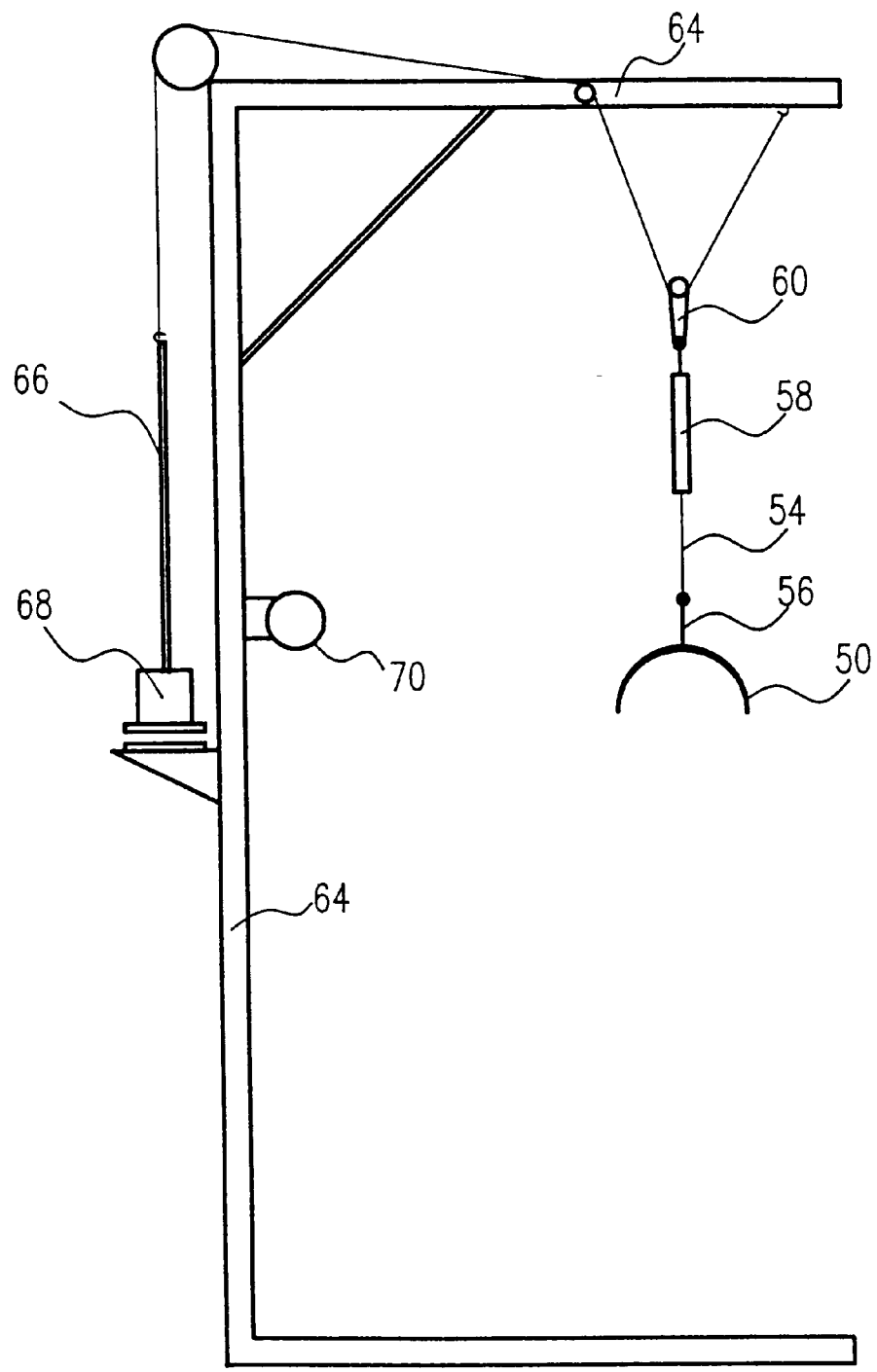
FIGS. 3a and 3b show schematic views of a countertraction mechanism for countering the inward pulling forces exerted during application of negative pressure within the domed vest wherein the configuration of FIG. 3a is used when the patient is lying on his or her back and the configuration of FIG. 3b is used when the patient is lying on his her side.
Figure 3B:
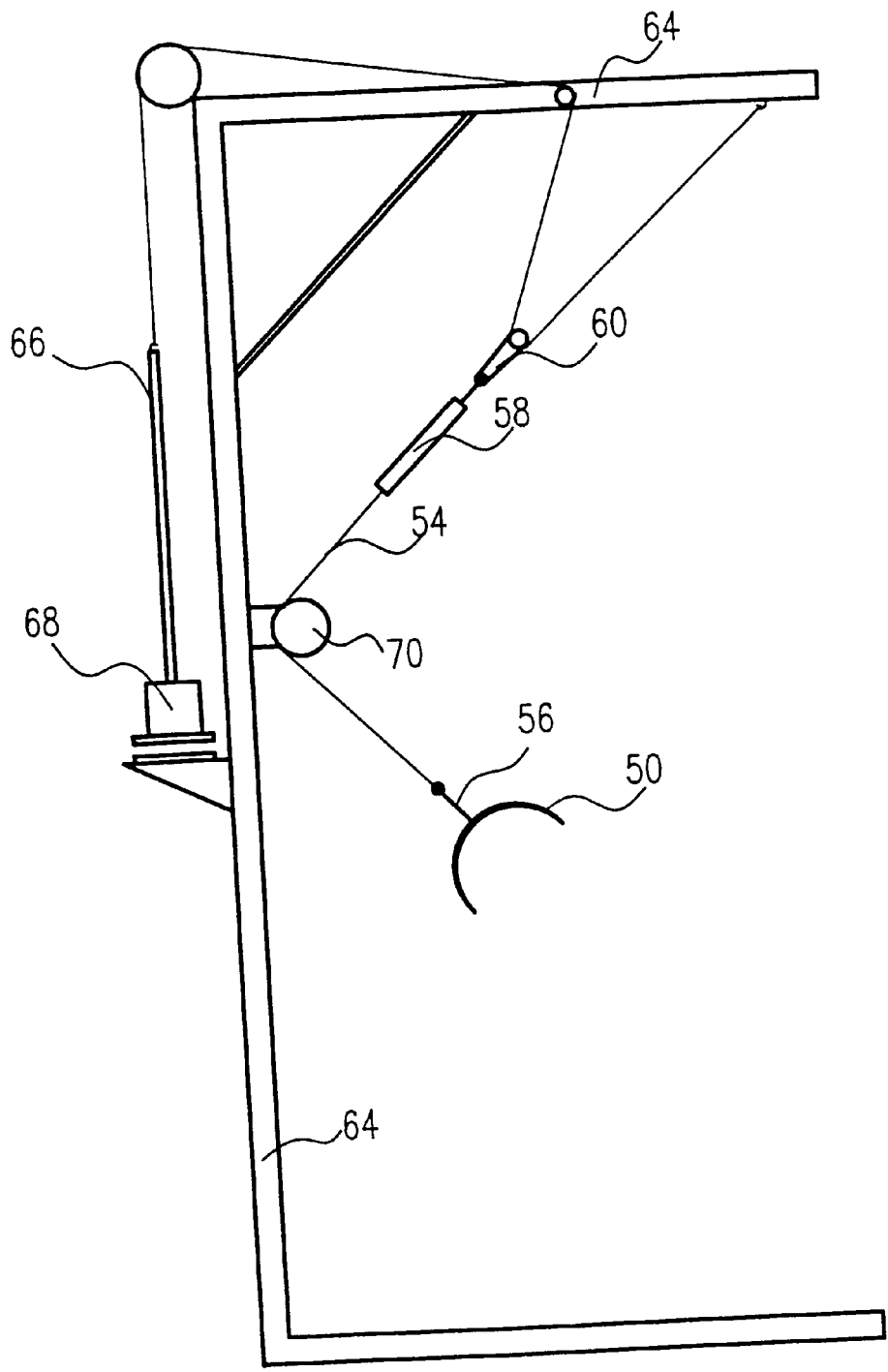

The mechanism for counteracting the downward pulling forces can take a variety of different forms. FIGS. 3a and 3b show one embodiment which utilizes counter-traction with a weight and pulley system. However, it should be understood that other mechanisms such as pneumatic drives, mechanical drives (e.g., gears), and the like might also be used. The objective of the counter-traction is to provide a means for reducing downward pull against the patient's body, but retaining the upward abdomen pulling forces of the vacuum pressure.

FIGS. 3a–b show a test counter-traction system which has been successfully used in clinical experiments. The shell 50, which fits over the patient's abdomen and operates in the same way as dome 30 in FIGS. 2a–b or covered frame 18 in FIGS. 1a–b, is fitted with a vacuum hose 52 which allows drawing a vacuum in the space between the inside of the shell 50 and the patient's body. A wire 54 is secured to the shell 50 by an anchor 56. The wire 54 extends to a spring-tension scale 58 which is connected to a pulley 60. The pulley 60 is positioned on a wire 62 positioned in a frame 64 cantileavered over the patient. The end of wire 62 is connected to a hanging platform 66 on which weights 68 can be positioned. By positioning different amounts of weight on the platform 66, various amounts of counter-traction force can be exerted on the shell 50.

In operation, vacuum pressure is exerted on the patient's abdomen inside the shell 50 via vacuum hose 52. To counteract the downward pulling force of the vacuum against the shell (which will draw the shell closer to the patient), weights 68 are placed on platform 66, and this exerts a force which pulls upward on shell 50. Weights 68 are preferably added in progressively increasing amounts until the maximum negative pressure in the space between the inside of the shell 50 and the patient's abdomen is reached without loss of the vacuum connection with the patient. In experiments to date, up to 18 Kg of negative counter-traction has been used as measured with the spring-tension scale 58.

FIG. 3b shows a particular advantage of the countertraction pulley mechanism in that it permits a person to lay on his or her side during use of the shell 50. This is accomplished by positioning wire 54 under a pulley 70 positioned on the upright portion of frame 64. In this configuration, the wire 54 is exerting a force directly away from the shell's 50 surface when the patient is laying on his or her side facing the frame 64. The ability to treat a patient laying flat or on his or her side can help alleviate patient discomfort, bed sores, pressure ulcers, and other clinical problems.

EXAMPLE 1

Pigs weighing approximately 70 kg have been studied using an abdominal decompression device similar to that shown in FIGS. 1a–b, which has been named an "ABSHELL", following experimentally induced increased intra-abdominal pressure and volume re-expansion. They were anesthetized and underwent an infusion of a polyethylene glycol solution (Go-Lytely) into their abdomen in order to increase their intra-abdominal pressure (IAP), as measured by urinary bladder pressure, to 25 mm Hg above baseline. This increased IAP was maintained for three hours. The normal fall in cardiac index associated with this increase in IAP was prevented by increasing the intravascular volume with Lactated Ringer's solution, in an attempt to mimic a chronic, compensated state of increased IAP as seen in both severe obesity and pre-eclampsia. The increased IAP and volume expansion was associated with a significant ($p<0.01$) increase in mean systemic arterial pressure, from $91\pm4$ to $126\pm3$ mm Hg. Application of the ABSHELL device at a pressure of –40 mm Hg for four hours was associated with a 12 mm Hg decrease ($p<0.01$) in IAP and fall ($p<0.01$) in mean systemic arterial pressure to $101\pm23$ mm Hg. The increased IAP was also associated with an increase ($P<0.01$) in intracranial pressure from $11\pm0.8$ to $21\pm1.9$ mm Hg; this decreased ($p<0.01$) to $15\pm0.8$ mm Hg following application of the ABSHELL. significant increases in central venous and femoral venous pressures were also noted with the increased IAP which also fell significantly with the use of the ABSHELL. The effects of the ABSHELL were noted immediately after it was turned on and remained effective throughout the four hour period of its application.

These data suggest that an increased IAP is responsible for systemic hypertension, chronic lower extremity venous stasis, and intracranial hypertension seen in both severe obesity and pre-eclampsia and that an ABSHELL device which lowers IAP will probably be of significant clinical benefit in both of these conditions, as well as acute abdominal compartment syndrome seen in some critically ill patient's.

EXAMPLE 2

Central obesity is associated with an increased risk of Type II diabetes and systemic hypertension, considered to be secondary to increased visceral fat metabolism or Syndrome X. This study was designed to determine if increased intra-abdominal pressure (IAP) is also associated with central obesity and could also contribute to the co-morbidity of obesity. Methods: Weight, body mass index (BMI), Co-morbid history, sagittal abdominal diameter (SAD), waist:hip (w:h) ratio and urinary bladder pressure (UBP), as an estimate of intra-abdominal pressure, were measured in 84 consecutive morbidly obese patients and 5 non-obese patients with ulcerative colitis. Morbidity was divided into problems which are probably secondary to increased intra-abdominal pressure [gastroesophageal reflux disease (GERD)], obesity hypoventilation, venous stasis, incisional hernia, and urinary incontinence) and quite possibly due to increased intra-abdominal pressure (hypertension and Type II diabetes) or are probably non-pressure related (gallstones, sleep apnea, chronic low back pain, degenerative joint disease). Results: UBP was greater in the obese than the non-obese ($18\pm0.7$ vs. $7\pm1.6$ cm $H_2O$, $p<0.001$) correlated with SAD ($r=0.67$, $p<0.001$) and was greater ($p<0.02$) in patients with, than those without, morbidity probably or possibly due to increased intra-abdominal pressure. The slope of the correlation lines between SAD and UBP were similar in both men and women. W:H ratio correlated with bladder pressure in men ($r=0.6$, $p<0.05$) but not in women ($r=-0.3$)

Patients with pressure related co-morbidity had higher bladder pressures than those without pressure related co-morbidity (p<0.01). With multiple logistic regression analysis, diabetes was significantly associated with increased intra-abdominal pressure.

These results indicate that increased SAD was associated with increased IAP, which contributed to obesity co-morbidity, including hypertension, Type II diabetes, GERD, obesity hypoventilation, incisional hernia and incontinence. W:H ratio was not a reliable indicator of IAP for women who may have both peripheral and central obesity. These results suggest that hypertension and Type II diabetes, i.e. Syndrome X, is secondary to increased intra-abdominal pressure, rather than to increased visceral adipose tissue metabolism. SAD is probably a more reliable indicator of central obesity than W:H ratio.

EXAMPLE 3

Morbid obesity is associated with a high incidence of renal dysfunction and systemic hypertension, which resolves in ⅔ of patients with weight loss. Clinical evidence suggests that chronic elevation of intra-abdominal pressure may play a role in causing both interrelated problems. The present study sought to clarify the association between elevated intra-abdominal pressure, hypertension and renal dysfunction. Methods: Anesthetized swine (n=6) had catheters inserted for installation of an isosmotic, polyethylene glycol solution into the peritoneal cavity and for measurement of intra-abdominal pressure and mean arterial pressure. Following baseline measurements intra-abdominal pressure was incrementally raised to 25 mm Hg above baseline At maximum intra-abdominal pressure the intravascular volume was expanded until cardiac index (CI) returned to baseline. Abdominal decompression (AD) was then performed. Plasma renin activity (PRA) and aldosterone (ALDO) levels were measured at each time point. A control group of pigs were studied without raising intra-abdominal pressure. In a second experiment canines (n=5) had their intra-abdominal pressure raised to 25 mm Hg above baseline over three weeks. The intra-abdominal pressure was maintained at 25 mm Hg above baseline for a further two weeks Arterial pressures were recorded weekly. Final measurements of all pressures were obtained at five weeks. A second group of control animals (n=5) underwent the same protocol but did not have their intra-abdominal pressure raised.
Results: Acute elevation of intra-abdominal pressure in swine led to a significant (p<0.05, ANOVA) increase in both PRA (0.8±0.3 to 24.6±5.5) and ALDO levels (6.9±1.6 to 17.8±4.2). Both PRA and ALDO levels remained constant in the control animals without an increased intra-abdominal pressure. Chronic elevation of intra-abdominal pressure in canines led to a significant (p<0.01) increase in systemic arterial pressure (162±8 vs. 120±3), mean arterial pressure (129±7 vs. 102±2, and diastolic arterial pressure (107±7 vs 86±2), at five weeks, compared to baseline and to control animals.

Chronic elevation of intra-abdominal pressure is associated with an increase in systemic arterial pressure. Acute elevation of intra-abdominal pressures cause increases in PRA and ALDO levels. Therefore, chronic elevation of intra-abdominal pressure, most commonly seen in the morbidly obese, may cause hypertension in these patients by altering the function of the renin-angiotensin-aldosterone system.

EXAMPLE 4

Central obesity is associated with Type II diabetes and hypertension, considered to be secondary to increased visceral fat metabolism, or syndrome X. Previous studies have suggested that these problems may be secondary to increased intra-abdominal pressure (IAP). Additional IAP related problems in obesity might include pseudotumor cerebri, obesity hypoventilation, gastroesophageal reflux disease, lower extremity venous stasis, and incisional hernia. It was hypothesized that the externally applied abdominal continuous negative pressure device (ABSHELL) of this invention could reverse this pathophysiology.
Methods: the shell type ABSHELL shown in FIGS. 2a/2b of this patent was applied for six hours to a 42 year old 144 kg man, BMI 53 Kg/m$^2$, 32 cm sagittal abdominal diameter, with obesity hypoventilation, sleep apnea, hypertension, Type II diabetes, and venous stasis. This ABSHELL device was much more comfortable for the patient and easier to apply than the poncho type device. Because of a good vacuum seal, no retention straps were required Urinary Bladder Pressure (UBP), mean systemic arterial pressure (SAP), central venous pressure (CVP), pulminary capillary wedge pressure (PCWP), cardiac index (CI), internal jugular vein cross-section diameter (IJVx-sect) and velocity (IJVV) with 2D doppler ultrasound, PaO$_2$, PaCO$_2$, renin, aldosterone, insulin, and glucose before, during and after ABSHELL.
Results: Table 1 presents the results of this experiment:

TABLE 1

|  | BEFORE ABSHELL | DURING ABSHELL | AFTER ABSHELL |
| --- | --- | --- | --- |
| UBP | 25 | 10 | 25 |
| SAP | 98 | 78 | 104 |
| CVP/PCWP | 18/26 | 11/15 | 19/26 |
| IJVx-Sect/IJVV | 13/12 | 7/24 | — |
| PaO$_2$/PaCO$_2$ | 76/49 | 81/41 | 75/43 |
| Renin/Aldosterone | 8.0/2.9 | 0.5/1.2 | 5.6/2.1 |

The results in Table 1 demonstrate that hypertension, pseudotumor cerebri, and obesity hypoventilation are secondary to increased IAP and support the beneficial effect of prospective use of the ABSHELL for patients with pseudotumor cerebri, obesity hypoventilation, gastro-esophageal reflux disease, lower extremity venous stasis, etc. The patient stated that he could breath much more comfortably and felt less bloated while in the device. This study with the shell-type device demonstrates the functionality and effectiveness of the shell-type design.

EXAMPLE 5

Five severely obese patients with systemic hypertension have been studied in the ABSHELL using a poncho arrangement with a cage placed within it (similar to FIGS. 1a–b). Four patients were in the device for six hours and one for three hours. All five patients stated that they felt much less short of breath in the ABSHELL. The patients' urinary bladder pressure was 22.6±2.4 in H$_2$O, range 19 to 28 cm H$_2$O (where normal is 7) prior to use of the ABSHELL. The negative applied pressure ranged from 20–35 mm Hg. In four of the five patients, urinary bladder pressures fell by 4–8 cm H$_2$O. The mean decline was to 16.9±4.2 in H$_2$O. Systemic blood pressure did not change, but the drop in abdominal pressure (as reflected in bladder pressure) was associated with an increase in urine output and urinary sodium excretion (naturesis) in each of the four patients in whom urinary bladder pressure fell. The mean change in urinary sodium was from 85±42 to 121±40 in mEq/hr during the ABSHELL which fell to 71±30 mEq/hr when the ABSHELL was turned off for all patients. These data are consistent with an increased venous return to the heart from the decreased intra-abdominal pressure and decreased intra-pleural pressure.

The one patient who had no change in urinary bladder pressure also had no increase in urinary sodium excretion. At the time of surgery, this patient's subcutaneous tissue measured 12 cm; whereas, the patients who responded had subcutaneous tissue measurements of 6–9 cm. Thus, it is likely that the patient whose bladder pressure failed to respond had a much heavier abdominal wall which would have required a stronger vacuum pump to lower this pressure.

It is expected that use of the ABSHELL through the night (e.g., approximately eight hours) would result in a significant decrease in intra-vascular volume which would lead to a decrease in systemic as well as pulmonary artery blood pressures. It should also improve arterial blood gases, as a reflection of improved pulmonary function.

EXAMPLE 6

It has been found that increased pleural pressure mediates the effects of elevated intra-abdominal pressure upon the central nervous and cardiovascular systems. As discussed above, morbidly obese patients have been shown to have increased intra-abdominal pressure. Some have pseudotumor cerebri which responds to surgically induced weight loss. It was hypothesized that some of the deleterious effects of increased intra-abdominal pressure are mediated by increased pleural pressure and that these effects include increased cranial pressure, altered systemic hemodynamics, and decreased cerebral perfusion pressure.

Methods: Anesthetized, ventilated swine had a balloon inserted into the peritoneal cavity and catheters placed to measure intracranial pressure, pleural pressure, central venous pressure, wedge pressure and mean arterial pressure. Following baseline measurements, intra-abdominal pressure was increased by incrementally inflating the balloon and parameters were re-measured thirty minutes after each increase. Group 1 (n=5) had intra-abdominal pressure raised to 25 mm Hg above baseline, then released. Group 2 (n=3) underwent sternotomy in order to prevent the increased pleural pressure with increased intra-abdominal pressure.

Results: Elevated intra-abdominal pressure caused an increase in pleural pressure (4.3±1.3 to 11.8±1.9), an increase in intracranial pressure (7.3±0.6 to 16.4±1.9), an increase in central venous pressure (6.6±0.7 to 10.7±0.9) and an increase in wedge pressure (9.0±0.6 to 14.3±0.8), whereas cardiac index (CI) (3.4±0.3 to 1.6±0.1) and cerebral perfusion pressure (75.6±3.6 to 62.0±6.8) decreased (all data having statistical significance of p<0.05, ANOVA). Abdominal decompression returned intracranial pressure and all hemodynamic parameters toward baseline and increased cerebral perfusion pressure (62.0±6.8 to 75.9±6.5). Sternotomy negated all effects of increased intra-abdominal pressure except decreased CI (2.5±0.4 to 1.2±0.1).

These results show that increased intra-abdominal pressure causes increased pleural pressure, intracranial pressure, central venous pressure and wedge pressure, and decreases cerebral perfusion pressure and CI. Prevention of increased pleural pressure negates the effects of elevated intra-abdominal pressure. Abdominal decompression restores all parameters towards baseline levels. The mediator of increased abdominal pressure's adverse effects upon the central nervous and cardiovascular systems appears to be an increase in pleural pressure which in turn increases central vascular pressures and impedes venous drainage of the cranial vault.

EXAMPLE 7

As discussed above, the ABSHELL, was modified with a counter-traction mechanism shown in FIGS. 3a–b to alleviate pressure pain on the patient's rib cage and pelvis. Two patients have been studied in the modified device. The pain previously noted with the ABSHELL was not present in either patient. In addition it was observed that the counter-traction mechanism provided an additional decrease in IAP (as determined by urinary bladder pressure measurements). Specifically, with the use of the counter-traction, urinary bladder pressurements decreased to 8–12 cm $H_2O$ pressure. This was associated with a decrease in cerebrospinal fluid pressure in one patient with pseudotumor cerebri, and blood pressure in one patient with systemic hypertension.

The above-studies suggest that the ABSHELL will lead to decreased intra-abdominal and pleural pressures, a decrease in intra-vascular volume, decreased systemic and pulmonary blood pressures, improved pulmonary function, decreased lower extremity venous stasis, and decreased intracranial hypertension in morbidly obese patients. Furthermore, the ABSHELL device should be of benefit to women with preeclampsia, pregnant women with small growth for gestational age babies, critically ill patients with increased intra-abdominal pressure as a result of an acute abdominal compartment syndrome, and patients with a head injury or space occupying brain lesion.

While the invention has been described in terms of its preferred embodiments, those skilled in the art will recognize that the invention can be practiced with modification within the spirit and scope of the appended claims.

I claim:

1. An abdominal decompression apparatus, comprising:

compartment for enclosing a space around a patient's abdomen;

means for applying negative pressure within said compartment; and a counter-traction means for countering negative pressure induced movement of said compartment towards the patient's abdomen.

2. The abdominal decompression apparatus of claim 1 further comprising a means for measuring the patient's urinary bladder pressure.

3. The abdominal decompression apparatus of claim 1 wherein said means for applying negative pressure applies a pre-selected negative pressure in said compartment continuously for a selected period of time.

4. The abdominal decompression apparatus of claim 3 wherein said pre-selected negative pressure ranges from −20 mm Hg to −45 mm Hg.

5. The abdominal decompression apparatus of claim 1 wherein said means for countering negative pressure comprises a pulling means connected to said compartment which exerts a pulling force on said compartment which is opposite said negative pressure induced movement of said compartment towards the patient's abdomen.

6. The abdominal decompression apparatus of claim 5 wherein said pulling means comprises a line connected to said compartment and a means to apply said pulling force to said line.

7. The abdominal decompression apparatus of claim 6 wherein said means to apply said pulling force allows variable amounts of said pulling force to be applied to said line.

8. The abdominal decompression apparatus of claim 6 wherein said means for applying a pulling force comprises a bearing member and a weight application member, said line extending over said bearing member and connected to said weight application member.

9. The abdominal decompression apparatus of claim 8 wherein said bearing member is a pulley.

10. The abdominal decompression apparatus of claim 8 further comprising a second bearing member positioned between said compartment and said bearing member, said line being selectively extendable over said second bearing member.

11. A method for performing abdominal decompression on a patient, comprising the steps of:

enclosing a space around a patient's abdomen with an air tight enclosure;

applying negative pressure in said space; and using a counter-traction mechanism to counter negative pressure induced movement of said air tight enclosure towards the patient's abdomen during said applying step.

\* \* \* \* \*